US007119167B2

(12) United States Patent
Moineau et al.

(10) Patent No.: US 7,119,167 B2
(45) Date of Patent: Oct. 10, 2006

(54) FRAGMENT OF L. LACTIS PLASMID CONFERRING ANTIPHAGE ACTIVITY AND USES THEREOF

(75) Inventors: Sylvain Moineau, Notre-Dame-du-Bon-Conseil (CA); Julie Bouchard, Cap-Santé (CA); Éric Dion, Loretteville (CA)

(73) Assignee: Université Laval, Québec (CA)

( * ) Notice: Subject to any disclaimer, the term of this patent is extended or adjusted under 35 U.S.C. 154(b) by 0 days.

(21) Appl. No.: 10/471,602

(22) PCT Filed: Apr. 5, 2002

(86) PCT No.: PCT/CA02/00503

§ 371 (c)(1),
(2), (4) Date: Apr. 2, 2004

(87) PCT Pub. No.: WO02/081697

PCT Pub. Date: Oct. 17, 2002

(65) Prior Publication Data

US 2004/0157312 A1 Aug. 12, 2004

Related U.S. Application Data

(60) Provisional application No. 60/281,415, filed on Apr. 5, 2001.

(51) Int. Cl.
*C07K 14/00* (2006.01)
*C07K 14/05* (2006.01)
*C07K 14/335* (2006.01)
*C07K 19/00* (2006.01)
*C12P 19/36* (2006.01)
*C12P 19/38* (2006.01)

(52) U.S. Cl. ............... 530/350; 536/23.1; 536/23.7; 536/23.72; 435/69.1; 435/91.1; 435/93.1; 435/243; 435/245; 435/252.2

(58) Field of Classification Search ............ 536/23.1, 536/23.7, 23.72; 530/350; 435/91.1, 69.1; 424/93.1, 93.2

See application file for complete search history.

(56) References Cited

U.S. PATENT DOCUMENTS

| 4,931,396 A | 6/1990 | Klaenhammer et al. |
| 5,019,506 A | 5/1991 | Daly et al. |
| 5,591,631 A * | 1/1997 | Leppla et al. ............ 435/252.3 |
| 5,593,885 A | 1/1997 | Klaenhammer et al. |
| 5,824,523 A | 10/1998 | Moineau et al. |
| 5,928,688 A | 7/1999 | Moineau et al. |
| 5,994,118 A * | 11/1999 | Moineau et al. ......... 435/252.9 |

FOREIGN PATENT DOCUMENTS

WO    WO 97 20917    6/1997

OTHER PUBLICATIONS

Sequence comparision results*
Allison G. E. et al., (1998) *Phage resistance mechanisms on lactic acid bacteria*, Int. Dairy J. 8: 207-226.
Moineau S., (1999) *Applications of phage in lactic acid bacteria*, Antonie van Leeuwenhoek 76: 377-382.
Bouchard J.D. et al., *Characterization of a novel phage resistance mechanism in Lactococcus lactis*, J. Anim. Sci., vol. 78, Suppl 1/J. Dairy Sci., vol. 83, Suppl. 1/2000.
O'Connor L. et al., *AbiG, a genotipically novel abortive infection machanism encoded by plasmid pCI750 of Lactococcus lactis subsp. Cremoris US653*, Applied and Envir. Microb. Washington D.C. US, col. 62, No. 9, Sep. 1996, pp. 3075-3082.
Su P et al., *Isolation, cloning and characterization of the abiI gene from Lactococcus lactis subsp. Lactis M138 encoding abortive phage infection*, J. of Biotechnology, Elsevier Science Publishers, Amsterdam, NL, vol. 54, No. 2, Apr. 25, 1997, pp. 95-104.
Brinboim, H. C., *A Rapid Alkaline Extraction Method for the Isolation of Plasmid DNA*, 1983, Method Enzym. 100:243-255.
O'Sullivan, D. J. et al., *Rapid Mini-Prep of High-Quality Plasmid DNA from Lactococcus and Lactobacillus spp.*, 1993 Appl. Environ. Microbiol. vol. 59, No. 8, 2730-2733.
Hill et al., *Rapid Method To Characterize Lactocuccal Bacteriophage Genomes*, 1991, Appl. Environ. Microbiol. vol. 57, No. 1, 283-288.
Altschul et al., *Gapped BLAST and PSI-BLAST: a new generation of protein search programs*, 1997, Nuc. Acids Res. 25 : 3389-3402.
Sanders el al., *Restriction and Modification in Group N Streptococci : Effect of Heat on Development of Modified Lytic Bacteriophage*, 1980, Appl. Environ. Microbiol. vol. 40, No. 3, 500-506.
Behnke et al., *Bacteriophage Interference in Streptococcus pyogenes*, 1978, Virology 85 : 118-128.
Moineau et al., *Differentiation of Two Abortive Mechanisms by Using Monoclonal Antibodies Directed toward Lactococcal Bacteriophage Capsid Proteins*, 1993, Appl. Environ. Microbiol. vol. 59, No. 1, 208-212.
Von Heijne G., *Membrane Protein Structure Prediction: Hydrophobicity Analysis and the Positive-inside Rule*, 1992, J. Mol. Biol. 225: 487-494.

(Continued)

*Primary Examiner*—Bao Qun Li
(74) *Attorney, Agent, or Firm*—Ogilvy Renault, LLP (57) ABSTRACT

The present invention relates to a 2227-bp DNA fragment that confers antiphage activity. Two proteins encoded by this DNA sequence are responsible for the phage resistance phenotype. When introduced in *Lactococcus lactis* phage-sensitive strain, this DNA fragment aborts infection of phages of the 936 and P335 species.

5 Claims, 7 Drawing Sheets

OTHER PUBLICATIONS

Holo H. et al., *High-Frequency Transformation, by Electroporation, of Lactococcus lactis subsp. Cremoris Grown woth Glycine in Osmotically Stabilized Media,* 1989, Appl. Environ. Microbiol. 55 : 3119-3123.

DATABASE EMBL Online EBI, Feb. 20, 1998, *Lactococcus lactis subsp. Cremoris plasmid pNZ4000, complete sequence,* Database accession No. AF036485 XP002207905.

DATABASE EMBL Online EBI, Aug. 10, 2000, *Lactococcus lactis subsp. Cremoris plasmid pAH82, complete sequence,* Database accession No. AF243383 XP 002207906.

GenBank database (accession No. AF483000).

* cited by examiner

FRAGMENT OF L. LACTIS PLASMID CONFERRING ANTIPHAGE ACTIVITY AND USES THEREOF

CROSS-REFERENCE TO RELATED APPLICATION

This application claims priority on U.S. provisional application Ser. No. 60/281,415 filed Apr. 5, 2001.

BACKGROUND OF THE INVENTION (a) Field of the Invention

The invention relates to DNA fragments encoding Abi-type proteins, determined herein respectively as AbiTi and AbiTii, which confers resistance to either naturally or artificially transformed bacteria against bacteriophages. The DNA fragments can be stably or transiently introduced, via a recombinant vector, into host fermentation bacteria. The invention encompasses isolated DNA fragments, recombinant vectors and transformed bacterial strains comprising the two AbiTi and AbiTii fragments.

(b) Description of Prior Art

*Lactococcus lactis* is a Gram-positive lactic acid bacterium used to acidify milk during the manufacture of cheese, sour cream and buttermilk. Lytic bacteriophages that attack *L. lactis* can slow down or completely inhibit the milk fermentation and are therefore responsible for substantial economic losses in the dairy industry. Naturally found in raw milk, they resist the pasteurization process, and can spread rapidly within a production plant as they have a short latent period and a relatively large outburst. *Lactococcal* phages are classified into twelve genetically distinct species. Three of them (936, P335 and c2) are the main cause of troubles since members of these species are regularly isolated worldwide.

Phages are always found in dairy environments and, therefore, the strategy is to control rather than eradicate them. Phage control relies on a variety of practical approaches ranging from adapted factory design, improved sanitation, adequate ventilation, processing changes, starter medium, culture rotation, and the use of phage-resistant starters.

Various techniques are available to protect the sensitive strains by transforming them into phage-resistant derivatives. The development of bacteriophage-insensitive mutant strains (BIM) was formerly the ideal method. A BIM is a spontaneous phage-resistant derivative that survives a long-term exposure to lytic phages, most likely as a result of a change in the phage receptor. Although this technique has the convenience of simplicity and rapidity, this natural evolutionary process is now rarely used for commercial Lactococcus strains due to substantial drawbacks including narrow phage-specificity, reversion of the resistance phenotype, and altered cell growth.

Decades of progress in the genetics of Lactococcus have established a solid basis for constructing another type of phage-resistant starters. Some *L. lactis* strains were found to naturally possess plasmids coding for anti-phage systems that can be transferred into industrial strains. These antiphage mechanisms are divided into four groups according to the moment of their action in the phage lytic cycle. Adsorption and DNA ejection inhibition mechanisms block respectively the first and second steps of the lytic cycle. Restriction/modification (R/M) systems cut the viral DNA once it has entered the cell. Finally, abortive infection (Abi) systems can act at any step between DNA ejection and cell lysis but their precise modes of action remain unknown. The resistance conferred by these natural lactococcal plasmids is often broad and effective against most phages of the same species. The discovery of these anti-phage barriers had a significant impact, as resistance strategies became based on phage species rather than on phage isolates (BIMS).

Phage resistant starter cultures have been successfully used for more than 15 years in industrial large-scale fermentation and many of anti-phage systems are subjected to limited exploitation. Over the same period, new phages have continued to emerge and the biodiversity of the phage population has never been so apparent. Unfortunately, some of these emerging phages are insensitive to the resistance mechanisms introduced into the industrial strains. Thus, there is a need for novel anti-phage systems.

The U.S. Pat. No. 5,994,118 describes a DNA encoding phage resistance protein. There is disclosed in this patent an Abi900 protein isolated from a natural 11 kb plasmid of *Lactococcus lactis*. The protein confers resistance to some bacteriophage infections.

The U.S. Pat. No. 4,931,396 describes a plasmid pTR2030 and derivatives thereof containing genetic determinants which confer phage resistance to group N streptococci. The plasmid has also a conjugal transfer phenotype upon expression in group N streptococci.

The U.S. Pat. No. 5,928,688 describes a DNA encoding phage resistance protein which aborts infection by the phage, designated as AbiE. The DNA, which is contained in a *Lactococcus lactis* deposited as NRRL-B-21443, is incorporated into a bacterium to encode the AbiE and provide phage resistance.

Antibacterial or antiviral systems are always offset by the emergence of resistant strains. Natural phage-resistant systems are not immuned to this evolutionary process.

It would be still highly desirable to be provided with modified or new phage-resistance factors, capable of conferring resistance to different bacteria used in fermentation processes.

SUMMARY OF THE INVENTION

One object of the present invention is to provide a modified or new phage-resistance factors, capable of conferring resistance to different bacteria used in fermentation processes.

Another object of the present invention is to provide an isolated polynucleotide encoding the protein as set forth in SEQ ID NO: 1 or SEQ ID NO:2, fragments or analogs thereof.

In accordance with the present invention there is provided a isolated protein comprising amino acid segment having an amino acid sequence as set forth in SEQ ID NO: 1 or SEQ ID NO:2, a fragment or an analog thereof.

In accordance with the present invention there is also provided an isolated polynucleotide encoding the protein as set forth in SEQ ID NO: 1 or SEQ ID NO:2, fragments or analogs thereof.

In accordance with the present invention there is also provided an isolated polynucleotide comprising at least one segment having the nucleotide sequence selected from the group consisting of SEQ ID NO:3, SEQ ID NO:4 and SEQ ID NO:5, fragments, homologues or combinations thereof.

In accordance with the present invention there is also provided an expression vector comprising at least one polynucleotide selected from the group consisting of SEQ ID NO:3, SEQ ID NO:4 and SEQ ID NO:5, fragments, homologues or combinations thereof In accordance with the present invention there is also provided bacterium transformed with a vector as previously described.

The bacterium may belong to *Lactococcus, Streptococcus, Lactobacillus, Leuconostocs, Pediococcus, Bifidobacterium, Oenococcus*, and *Propionibacterium*.

In accordance with the present invention there is also provided bacterium transformed with a vector containing a DNA encoding at least one polypeptide having a sequence selected from the group consisting of SEQ ID NO:1, and SEQ ID NO:2, fragments, homologues, or combinations thereof.

In accordance with the present invention there is also provided a method of conferring phage resistance to bacteria comprising introducing into bacteria vector encoding a protein, said protein having an amino acid sequence as set forth in SEQ ID NO:1 or SEQ ID NO:2, fragment, analogs or combination thereof.

The vector of the invention may be a plasmid.

Another object of the present invention is the use of a protein as defined by SEQ ID NO: 1 and 2 in the manufacture of a composition conferring phage resistance.

Also, one object of the present invention is the use of DNA sequences as defined by SEQ ID NO: 3 to 5 in the preparation of a transformed microorganism for conferring phage resistance to said microorganism.

For the purpose of the present invention the following terms are defined below.

The term "fragment" as used herein means any portion of a sequence encoding for AbiTi and/or AbiTii, and having a viral abortive activity.

The term "analog" as used herein is intended to mean any genetically, biochemically, chemically, or enzymatically modified form of the polypeptides AbiTi and AbiTii having an viral abortive activity.

The term "polypeptide" as used herein is intended to encompass a protein, a peptide, a polypeptide, a peptide chain, and an amino acid sequence of at least 5 amino acids.

The term "vector" as used herein refers to a nucleic acid, e.g., DNA derived from a plasmid, cosmid, plasmid, artificial chromosome or bacteriophage or synthesized by chemical or enzymatic means, into which one or more fragments of nucleic acid may be inserted or cloned which encode for particular genes. The vector can contain one or more unique restriction sites for this purpose, and may be capable of autonomous replication in a defined host or organism such that the cloned sequence is reproduced. The vector may have a linear, circular, or supercoiled configuration and may be complexed with other vectors or other material for certain purposes. The components of a vector can contain but is not limited to a DNA molecule incorporating DNA; a sequence encoding a reprogramming or another product; and regulatory elements for transcription, translation, RNA stability and replication. The expression "recombinant vector" as used herein is intended to mean in which are presents DNA fragments encoding for at least one phage-resistance protein all concurrently or either under control of a promoter and other transcription regulatory elements inducing the expression of a genes when the recombinant vector is introduced into a host microorganism.

DETAILED DESCRIPTION OF THE INVENTION

In accordance with the present invention, there is provided a DNA fragment containing two synergetic fragments AbiTi and AbiTii, which confer resistance to bacteriophages when expressed in bacteria transformed with recombinant vector containing two fragments encoding of AbiTi (SEQ ID NO:1) and AbiTii (SEQ ID NO:2) polypeptides.

Subfragments, portions, or mutated forms of AbiTi and AbiTii encoding sequences are embodiments of the present invention. Proteins and peptides encoded by transcription of these subfragments, portions, or analog forms of AbiTi and AbiTii are also parts of the present invention.

The invention further relates to a phage resistant lactic acid bacteria, preferably belonging to the species *Lactococcus lactis*, which contain at least one of the nucleic acid sequences or one plasmid as defined below.

These nucleic acid sequences or these plasmids may have been introduced into bacteria by conjugation, transformation, protoplast fusion or any other gene transfer method well known to those skilled in the art.

In one embodiment, a recombinant vector containing the two fragments AbiTi (SEQ ID NO:4) and AbiTii (SEQ ID NO:5) is used to confer phage-resistance to lactic acid bacteria, naturally or artificially transformed. Also, the encoding fragments AbiTi and AbiTii may further be contained in separated plasmid vectors, by being simultaneously introduced and expressed in the same bacteria.

In another embodiment of the present invention, the lactic acid bacteria may be advantageously transformed with the DNA sequence according to the invention as disclosed in SEQ ID NO:3, SEQ ID NO:4, or SEQ ID NO:5.

In another embodiment of the present invention, the bacterial strain transformed may be used for transmitting a phage resistance mechanism to a strain of industrial interest by conjugation, transformation, transduction, protoplast fusion or any other gene transfer method well known to those skilled in the art. This mechanism can be carried by a plasmid or by another part of the bacterial genome. If it is carried by a plasmid, it is advantageously transferred by conjugation.

The invention further relates to the phage resistant strains of industrial interest thus obtained.

In one embodiment of the present invention, bacterial strains that can be usefully transformed with recombinant vectors in accordance with the invention may be selected from the group consisting of *Lactococcus, Streptococcus, Lactobacillus, Leuconostocs, Pediococcus, Bifidobacterium, Oenococcus*, and *Propionibacterium*.

Figure 1:
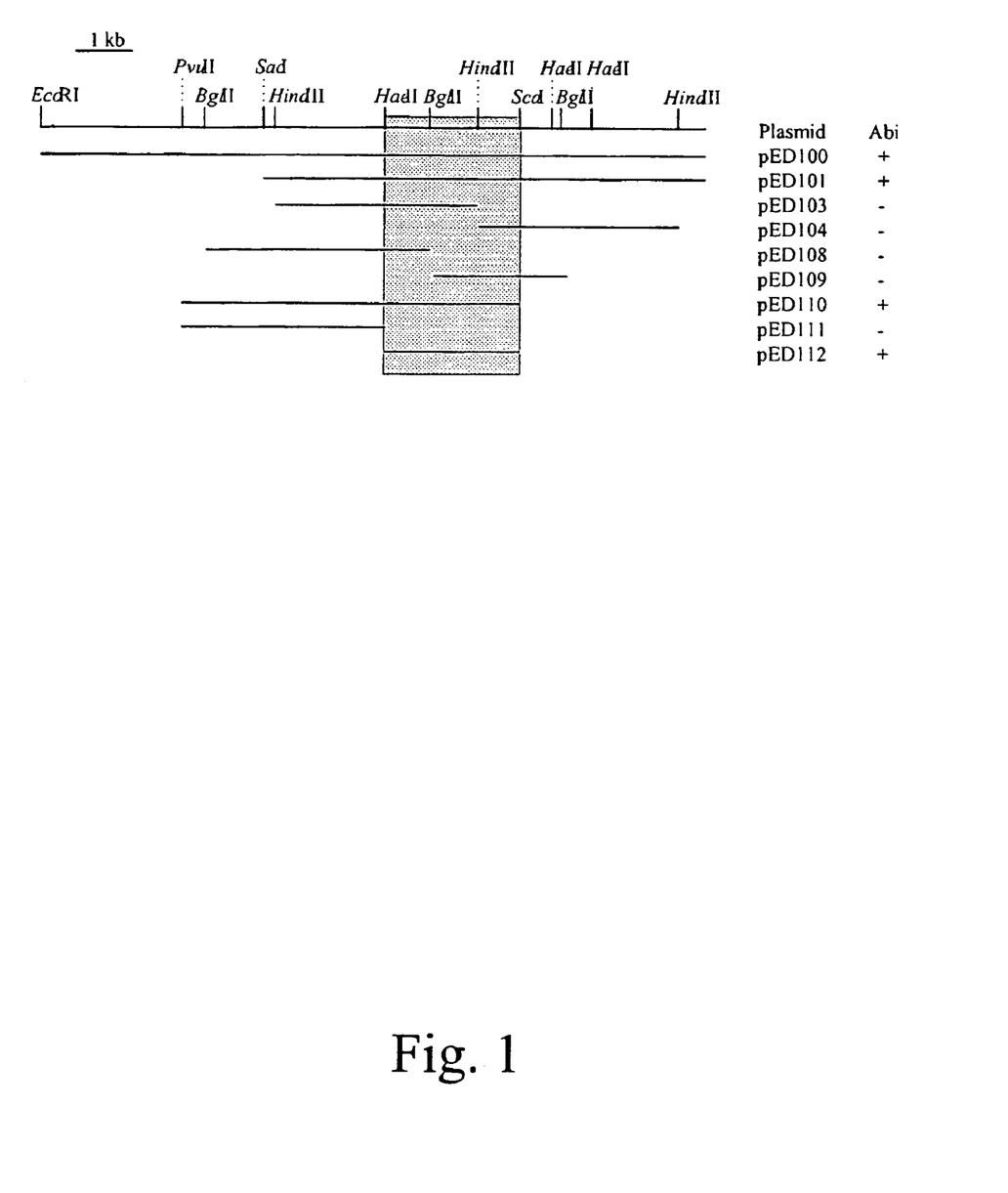
FIG. 1 illustrates the restriction map and subcloned fragments of the natural DNA fragment isolated from *Lactococcus lactis*.

More particularly, a DNA fragment of the present invention consists of a 2227-bp DNA fragment (SEQ ID NO:3) isolated from the *L. lactis* strain W51. A plasmid vector pED1 containing this DNA fragment may be introduced into a phage-sensitive *L. lactis* strain and tested for phage resistance. All phage-resistant colonies therefor contain a 12.2-kb plasmid named pED1. This plasmid is subcloned into a vector for *L. lactis* and a 2227-bp HaeII-ScaI restriction fragment is the smallest restriction fragment tested that could confer phage resistance (FIG. 1). Introduction of this DNA sequence into various phage-sensitive strains causes a diminution of the efficiency of plaquing (EOP) of phages belonging to two of the three most common species found in the dairy industry (936 and P335) (Table 1).

Figure 2:
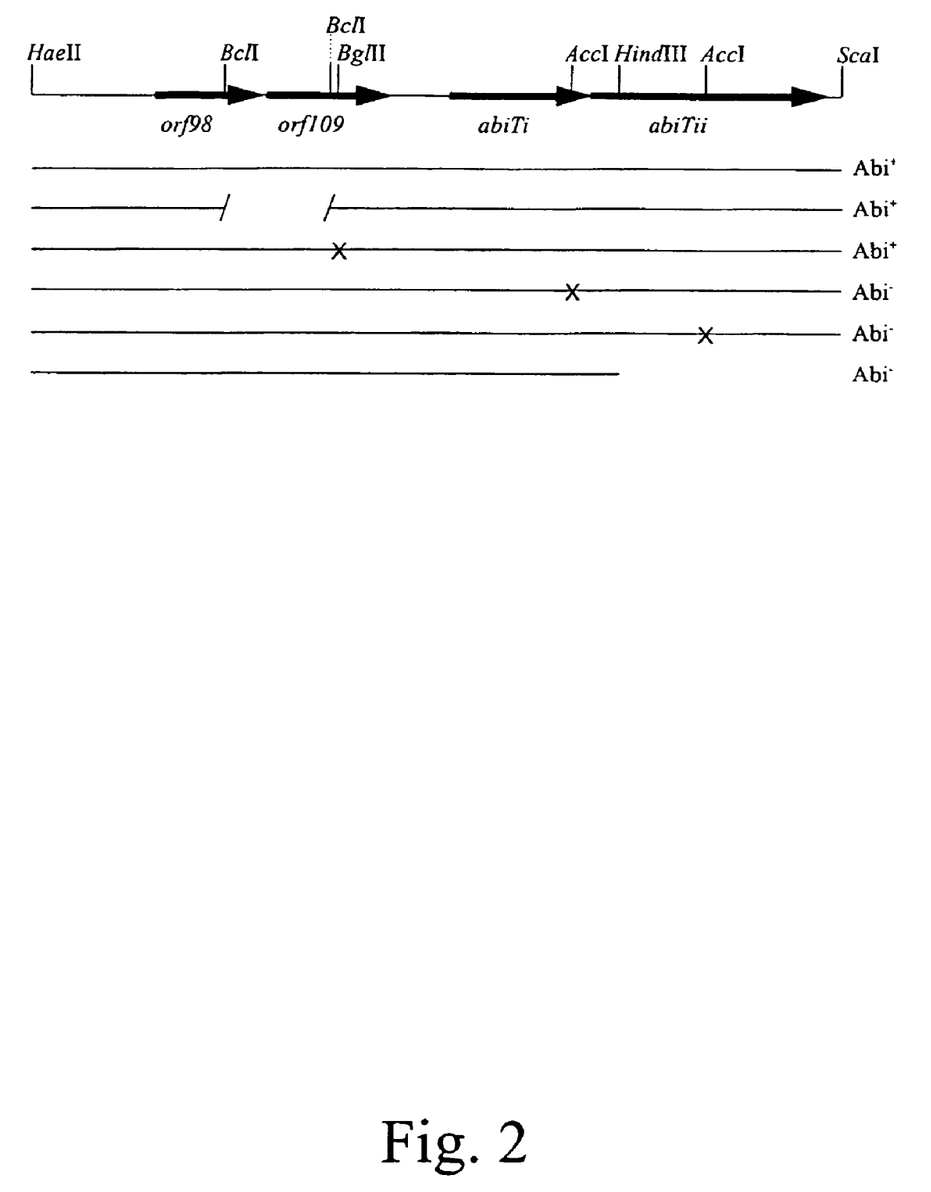
FIG. 2 illustrates the genetic organization of the 2227 bp DNA fragment of plasmid pED1 encoding the phage resistance mechanism AbiT of the present invention.
Figure 3:
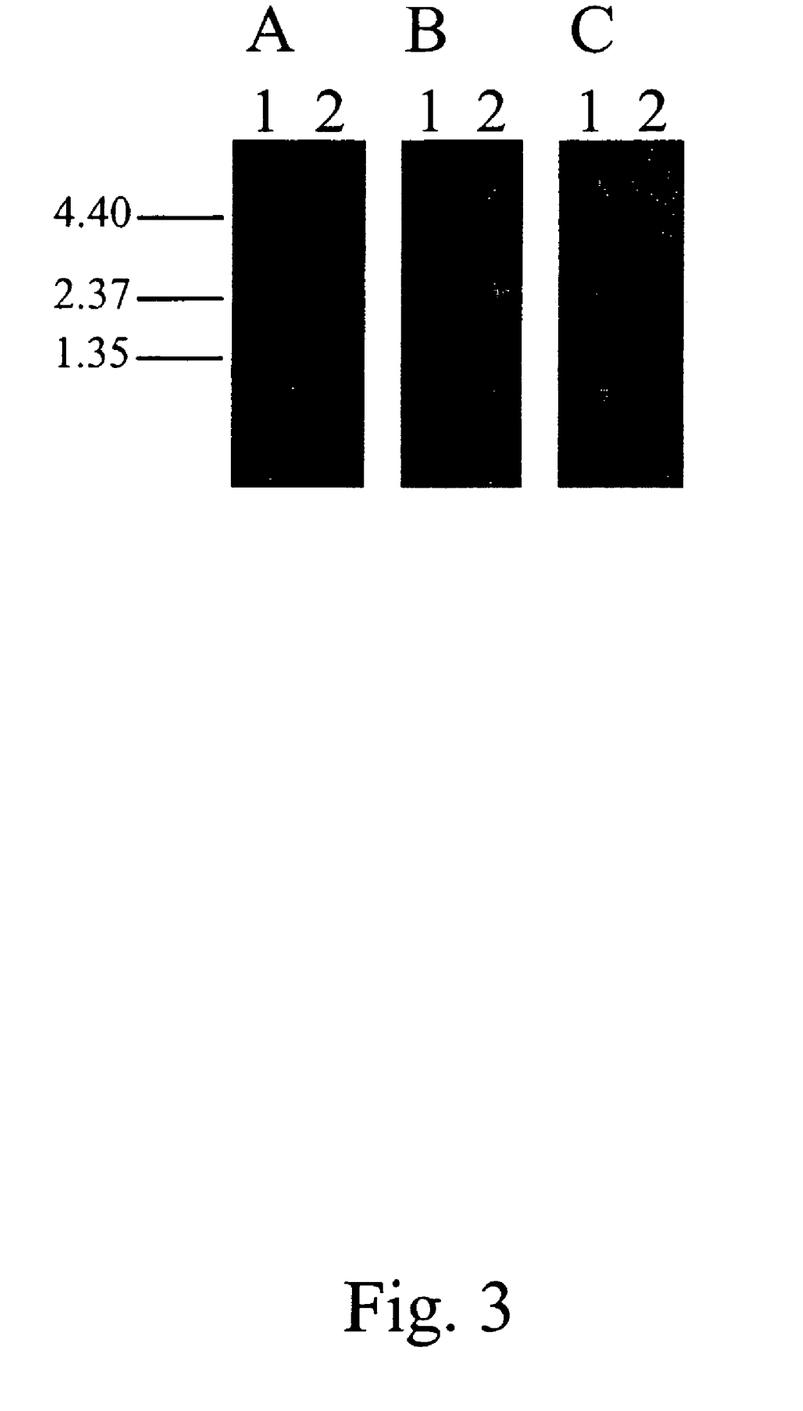
FIG. 3 illustrates Hybridization of RNA isolated from AbiT—containing *L. lactis* strains with labeled DNA fragment of abiTi (A), abiTii (B) and orf98-orf109 (C)

The DNA fragment contains four genes: orf98, orf109, AbiTi, and abitT2 (FIGS. 2 and 3). Inactivation of AbiTi and AbiTii resulted in the loss of the anti-phage activity. These two genes encode proteins of 127 (SEQ ID NO:1) and 213 (SEQ ID NO:2) amino acids that share no homology with any known nucleic acid sequences found in databases.

The present invention will be more readily understood by referring to the following examples that are given to illustrate the invention rather than to limit its scope.

EXAMPLE I

Activity of AbiTi and AbiTii

TABLE 1

Efficiency of plaquing (EOP) of phages belonging to the three most common phage species in the dairy industry on strains containing AbiT

| 936 species | | P335 species | | c2 species | |
|---|---|---|---|---|---|
| phage | EOP | phage | EOP | phage | EOP |
| p2 | $9.5 \pm 3.9 \times 10^{-6}$ | ul36 | $2.6 \pm 1.5 \times 10^{-7}$ | c2 | 1.0 |
| p2k | $1.4 \pm 0.6 \times 10^{-6}$ | Q30 | $1.6 \pm 0.4 \times 10^{-7}$ | ml3 | 1.0 |
| sk1 | $2.1 \pm 1.4 \times 10^{-5}$ | phi31 | $1.9 \pm 0.8 \times 10^{-7}$ | eb1 | 1.0 |
| jj50 | $1.9 \pm 0.8 \times 10^{-5}$ | phi50 | $4.5 \pm 3.4 \times 10^{-6}$ | | |

Anti-viral systems in *L. lactis* are currently classified in four groups based on their general mode of action: adsorption blocking, DNA ejection blocking, restriction/modification (R/M), and abortive infection systems. Phages adsorption is not inhibited by the presence of the 2227-bp DNA fragment (Table 2). Phage DNA replication is observed in cells carrying this anti-phage system indicating that the phage DNA is ejected within the cells despite the presence of the 2227-bp DNA fragment. Phages isolated in presence of the anti-phage mechanism are permanently insensitive to it indicating that it is not a R/M system. Finally, cell death is observed following phage infection of cells carrying the 2227-bp DNA fragment, a characteristic of abortive infection systems (Table 2). Therefore, these results demonstrate that this anti-phage system is an abortive infection mechanism and was named AbiT⁻.

TABLE 2

Microbiological effects of AbiT on phages p2 and ul36

| | p2 (936 species) | | ul36 (P335 species) | |
|---|---|---|---|---|
| | AbiT⁻ | AbiT⁺ | AbiT⁻ | AbiT⁺ |
| ECOI (%) | 100 | $6.8 \pm 3.5$ | 100 | $4.5 \pm 1.2$ |
| Burst size | $58 \pm 14$ | $6 \pm 2$ | $342 \pm 28$ | $27 \pm 6$ |
| Adsorption (%) | $93 \pm 3$ | $96 \pm 2$ | ND | ND |
| Cell survival (%) | $11 \pm 4$ | $16 \pm 6$ | ND | ND |

ND, not determined

The plasmid pED1 that contain and is capable of exressing the DNA sequences AbiTi and AbiTii, can be introduced into industrial strains of *L. lactis* or other lactic acid bacteria to prevent phage proliferation in dairy plants. The 2227-bp HaeII-ScaI fragment, which is sufficient to impart phage resistance, could also be cloned in a plasmid vector to achieve this goal.

EXAMPLE II

Abortive Phage Infection Mechanism AbiT from *Lactococcus lactis*

Materials and Methods

Bacterial Strains, Plasmids, and Media

Strains and plasmids used in this study are listed in Table 3. *E. coli* was grown at 37° C. in LB medium and *L. lactis* was grown at 30° C. in M17 (Quélab) supplemented with 0.5% glucose (GM17) or, in the case of W51, with 0.5% lactose (LM17). When needed, antibiotics were added to the media at the following concentrations: 50 µg of ampicillin per ml or 20 µg of chloramphenicol per ml for *E. coli* and 5 µg of chloramphenicol or erythromycin per ml for *L. lactis*.

Bacteriophage Propagation and Microbiological Assays

Bacteriophages used in this study are listed in Table 3. The efficiency of plaquing (EOP) was calculated by dividing the phage titer on the tested strain by the titer on the sensitive control strain. Adsorption assays were conducted as described by Sanders and Klaenhammer (1980, Appl. Environ. Microbiol. 40:500–506) and cell survival was assayed by the method of Behnke and Malke (1978, Virology, 85:118–128). One-step growth curves were performed as described previously (Moineau ete al., 1993, Appl. Environ. Microbiol. 59:208–212).

TABLE 3

Strains, plasmids and bacteriophages used in this study

| Strain, plasmid or phage | Relevant characteristics[a] |
|---|---|
| *L. lactis* | |
| W51 | Multiple plasmids, including pED1 |
| LM0230 | Plasmid-free host for 936- and c2-like phages |
| MG1363 | Plasmid-free host for 936- and c2-like phages |
| SMQ481 | Host for P335-like phages |
| *E. coli* | |
| DH5alpha | Cloning host |
| GM48 | dam⁻/dcm⁻ host |
| Plasmids | |
| pBS | Cloning vector for DNA sequencing, Ap^r, 2.9 kb |
| pSA3 | *E. coli* - *L. lactis* shuttle vector, Cm^r, Tc^r, Em^r, 10.2 kb |
| pMIG3 | *E. coli* - *L. lactis* shuttle vector, Cm^r, 5.5 kb |
| pNZ123 | High copy vector for *L. lactis*, Cm^r, 2.8 kb |
| pMG36c | Expression vector for *L. lactis*, Cm^r, 3.4 kb |
| pED1 | Resident plasmid of W51, Abi⁺, 12.2 kb |
| Bacteriophages | |
| p2 | 936 species, small isometric headed, cos-type |
| p2k | 936 species, small isometric headed |
| sk1 | 936 species, small isometric headed |
| jj50 | 936 species, small isometric headed |
| ul36 | P335 species, small isometric headed, pac-type |
| Q30 | P335 species, small isometric headed |
| Q33 | P335 species, small isometric headed |
| ☐31 | P335 species, small isometric headed |
| ☐50 | P335 species, small isometric headed |
| c2 | c2 species, prolate headed |

TABLE 3-continued

Strains, plasmids and bacteriophages used in this study

| Strain, plasmid or phage | Relevant characteristics[a] |
|---|---|
| eb1 | c2 species, prolate headed |
| ml3 | c2 species, prolate headed |

[a]Ap[r], ampicillin resistance;
Cm[r], chloramphenicol resistance;
Tc[r], tetracycline resistance;
Em[r], erythromycin resistance;
AbiT[+], active abortive infection mechanism.

The efficiency to form centers of infection (ECOI) was calculated by dividing the phage titer, obtained with resistant infected cells, by the titer obtained with the sensitive strain immediately after the adsorption step. The burst size was determined by dividing the average titer after the exponential phase by the average titer before cells began to release virions. The phage lytic cycle was monitored at time intervals by electron microscopy in AbiT[−] and AbiT[+] strains.

DNA Isolation and Manipulations

E. coli plasmid DNA was isolated by the method of Birnboim (1983, Metehods Enzym. 100:243–255). L. lactis plasmid DNA was isolated as described by O'Sullivan and Klaenhammer (1993, Appl. Environ. Microbiol. 59:2730–2733). Phage DNA was prepared as described previously (40) and large amounts were obtained with the Qiagen Lambda Maxi Kit (Qiagen). Total intracellular DNA was isolated by the method of Hill et al. (1991, Appl. Environ. Microbiol. 57:283–288). E. Coli was transformed with the Gene Pulser II apparatus as indicated by the manufacturer and L. lactis electrotransformation was done as specified by Holo and Nes (1989, Appl. Environ. Microbiol. 55:3119–3123).

DNA Sequencing and Sequence Analysis

Fragments were cloned in pBS and sequenced on both strands with an ABI Prism 3100 apparatus using the universal forward and reverse primers as well as synthetic primers (Invitrogen). DNA and deduced protein sequences were analyzed with the Wisconsin Package Version 9.0 (Genetics Computer Group). The open reading frames were compared with the available databases using BLAST version 2.1.1 (Altschul et al., 1997, Nuc. Acids Res. 25:3389–3402). The DNA sequence was deposited in the GenBank database (accession no. AF483000).

Plasmid Construction

DNA fragments from pED1 cloned into the cloning vectors pMIG3, pNZ123 and pSA3 were designated by the prefix pED1XX, pED2XX and pED3XX, respectively. The XX correspond to the DNA fragments presented in FIG. 1 or in Table 5. When needed, pBS was first used to clone restriction fragments and to introduce deletions or frameshifts, as it contains more convenient restriction sites. The abiT genes were amplified using primers containing restriction sites (in bold) to generate pED418 and pED419 (primers PED1.1, 5'-GAATTCGAATTCGATTATAAGAAACG-GAGGGAC-3' (SEQ ID NO: 6) and PED1.2, 5'-TCTAGATCTAGACCGTTTTCGTAGTATCACGT-3' (SEQ ID NO:7)) as well as pED107 and pED307 (primers PED1.2 and PED1.3, 5'-GTCGACGTCGACGGT-GCTTTTTGTCTTTCTAGTT-3' (SEQ ID NO:8)). Site-directed mutagenesis was done by the megaprimer PCR method. The mutagenic primers (mutation in bold) are the following: R108T, 5'-GCTACTTGTAACTGTTAAT-GATATG-3' (SEQ ID NO:9); A115E, 5'-TTCCTGTTTC-CACTAAGCTACT-3' (SEQ ID NO:10); A115V, 5'-TTCCT-GTTACCACTAAGCTACT-3' (SREQ ID NO:11); L122R, 5'-ACTTGACTACGTAGACCAAGTA-3' (SEQ ID NO:12); L112P, 5'-ACTTGACTAGGTAGACCAAGTA-3' (SEQ ID NO: 13).

RNA Isolation and Manipulations

Cells were grown in 100 ml of GM17 at an O.D. of 0.2 and pelleted. For phage RNA isolation, the following steps were added: the pellet was resuspended in 10 ml of GM17 with $CaCl_2$ at 10 mM and phage was added at a multiplicity of infection of 1. Aliquots of 1 ml were taken at different time points, mixed with 100 μl of rifampicin at 10 mg/ml, centrifuged, and the pellet was immediately frozen at −80° C. Total RNA was isolated with the RNeasy Mini Kit (Qiagen) according to the manufacturer's instructions. After a treatment with RNase-free DNase I (Roche Diagnostic), 4 μg of each RNA sample were migrated on a formaldehyde gel and transferred to a nylon membrane as described by Sambrook and Russell (46). The following DNA fragments were labeled with [α-$^{32}$P]dATP (Amersham Pharmacia Biotech) by random-priming and used as probes: the 256-bp BcII fragment of pED1 for orf98 and orf109, PCR products corresponding to abiTi and abiTii (coordinates 1233–1534 and 1599–2202), to the orf35-homologue and the mcp gene of p2 (coordinates 20478–21179 and 6837–7259 in sk1, accession no. AF011378).

Results

Plasmid Isolation and Classification of the Antiphage Mechanism

Lactococcus lactis W51 was previously isolated from raw milk and was shown to be resistant to a cocktail of phages. However, this strain produces off-flavors when cultivated in milk, thereby preventing its use in commercial applications. We set forth to determine the mechanisms responsible for the phage resistance phenotype in L. lactis W51. The cryptic plasmids of W51 were co-electroporated with the plasmid vector pSA3 (containing an erythromycin resistance gene) into the phage-sensitive, plasmid-free strain LM0230 (Table 3). Colonies isolated on erythromycin-containing media were then tested for phage resistance with phage p2 of the 936 species. All phage-resistant isolates contained, in addition to pSA3, a 12.2-kb plasmid named pED1. Curing of pSA3 produced an erythromycin-sensitive phage-resistant strain, which confirmed the involvement of pED1 in the antiphage activity.

The efficiency of plaquing (EOP) of the small isometric-headed phage p2 (936 species) on LM0230 (pSA3, pED1) was of $10^{-6}$ at 20, 30, and 39° C. Plaques isolated on the strain remained insensitive to the antiphage mechanism after propagation through a sensitive host, which demonstrates that it is not a restriction/modification system. Plasmid pED1 did not affect the first step of the phage lytic cycle since the adsorption of phage p2 was of 93±3% on LM0230 (pSA3) and of 96±2% on LM0230 (pSA3, pED1). Finally, cell survival was of 11±4% for the sensitive strain and of 16±6% for the pED1-containing strain. The fact that resistant cells do not survive phage infection proves that the antiphage system carried by pED1 is an abortive infection mechanism. It was therefore named AbiT.

Cloning and Identification of the Genetic Determinants of AbiT

Plasmid pED1 was subcloned into the shuttle vector pMIG3 after restriction mapping. The different clones were then introduced into the plasmid-free phage-sensitive L. Lactis MG1363 and their Abi phenotype was tested with phage p2. The 2.2-kb HaeII-ScaI fragment was the smallest region that conferred phage resistance (FIG. 1). This restriction fragment was cloned in pBS for DNA sequencing. Bioinformatic analysis revealed that it comprises four open reading frames (ORFs) (Table 4, FIG. 2) preceded by a putative promoter (coordinates 234–262, TTGTAG-17nt-AATAAT). Since no transcription terminator could be identified on the 2.2-kb HaeII-ScaI fragment, the 2.7-kb HaeII fragment was entirely sequenced (FIG. 1). Two inverted repeats (coordinates 2225–2252 and 2264–2288) and a stretch of 7 T nucleotides (2289–2295) that could act as a rho-independent terminator (G=−22.2 kcal/mol) were localized immediately after the ScaI site. The four putative genes are therefore organized as an operon.

The sequenced region of 2711 bp had a G+C content of 32.3%. Its 5' and 3' regions (coordinates 1–960 and 2620–2711) had more than 90% identity at the DNA level with the lactococcal plasmids pNZ4000 and pAH82 (FIG. 2). Another segment (coordinates 2302–2562) had 89% identity with Tn916 of *Enterococcus faecalis* (Accession no. U09422) and Tn5251 of *Streptococcus pneumoniae* (Accession no. X90941). The different ORFs were inactivated by the introduction of deletions or frameshifts and only orf127 and orf213 were necessary to obtain an Abi⁺ phenotype (FIG. 2). They were renamed abiTi and abiTii. Deletion of the putative promoter also resulted in the loss of the phage resistance phenotype.

transcript of about 2 kb was observed with pED100 and pED107 (FIG. 1, FIG. 2 and FIG. 3). Transcripts containing the genetic determinants of AbiT, but not the putative terminator, were of various lengths. This confirms the location and function of the predicted terminator.

Site-Directed Mutagenesis of AbiTi

The putative AbiTii protein does not contain a particular motif. However, the putative AbiTi protein has a hydrophobic region at its C-terminal extremity (residues 107–127, Table 5). To determine whether this region is essential to the antiphage phenotype, two of the hydrophobic residues were replaced by a proline, a charged residue or a different hydrophobic residue by site-directed mutagenesis. Clones containing wild-type or mutant abiTi and wild-type abiTii were confirmed by DNA sequencing and tested for their ability to abort phage p2 infection. Replacement of A115 and L122 by a proline or a charged residue resulted in the loss of the anti-phage activity, while mutant A115V was as phage resistant as the wild-type strain (Table 5). Substitution of R108, the first charged residue upstream of the hydrophobic region, by a threonine reduced partially the efficacy of AbiT. DAS, TMpred, and Toppred2 programs (von Heijne, 1992,

TABLE 4

Characteristics of the ORFs of the sequenced 2.2-kb HaeII-ScaI fragment of plasmid pED1 that conferred phage resistance

| ORF | Start | Stop | % G + C | MW (kDa) | pI | SD sequence AGAAAGGAGGA (SEQ ID NO:14) | Similarity | % of identity (aa) | Access. no. |
|---|---|---|---|---|---|---|---|---|---|
| 98 | 352 | 648 | 24.9 | 11.7 | 4.39 | AAAAGAGAGGA (SEQ ID NO:15) | pAH82 (orf3) | 100 (98/98) | AF243383 |
|  |  |  |  |  |  | ttctcaaATG (SEQ ID NO:16) | pNZ4000 (orf98) | 100 (98/98) | AF036485 |
| 109 | 677 | 1006 | 47.9 | 12.5 | 9.35 | Non identified | pCI305(orf3b) | 94 (92/97) | AF179848 |
|  |  |  |  |  |  |  | pCI305(orf3a) | 90 (87/96) |  |
|  |  |  |  |  |  |  | pNZ4000 (orf154) | 90 (87/96) | AF036485 |
|  |  |  |  |  |  |  | pAH82 (orf4) | 90 (87/96) | AF243383 |
|  |  |  |  |  |  |  | pCD4 (orfA) | 90 (87/96) | AF306799 |
|  |  |  |  |  |  |  | pSRQ800 (orfA) | 91 (87/95) | U35629 |
|  |  |  |  |  |  |  | pSRQ900 (orfA) | 90 (87/96) | AF001314 |
| 127 (abiTi) | 1175 | 1558 | 33.1 | 14.1 | 5.67 | AGAAACGGAG (SEQ ID NO:17) GgacattATG (SEQ ID NO:18) | Unknown |  |  |
| 213 (abiTii) | 1569 | 2210 | 31.2 | 24.4 | 5.00 | GAGGtagtacaATG (SEQ ID NO:19) | *Xylella fastidiosa* (gene XF2427) | 28 (54/188) | AE004052 |

Expression of AbiT

To confirm that the first 585 bp of the HaeII fragment included the promoter required for phage resistance, abiTi and abiTii were cloned as a PCR product (coordinates 1151–2313) in both orientations in the lactococcal expression vector pMG36c. The two constructs (pED419 and pED420) were introduced into MG1363 and their effect on phage p2 was tested. When cloned in the sense orientation (pED419), the two genes affected phage proliferation, whereas no antiphage activity was observed in the antisense orientation (pED420). Thus, the 5' region of the fragment can be replaced by a constitutive promoter of *L. lactis*.

To determine whether abiTi and abiTii are constitutively expressed from their own promoter and are located on the same transcript, total RNA of MG1363 containing pertinent subclones of pED1 was isolated. Following separation on gel and Northern blotting, RNA was hybridized with DNA fragments internal of each of the abiT genes and with a fragment covering orf98 and orf109. The hybridization patterns were identical for all probes (FIG. 3), which demonstrates that abiTi and abiTii are co-expressed. A unique J. Mol. Biol. 225:487–494) predicted this segment of AbiTi as a transmembrane helix, but could not predict its orientation. Translational fusions between AbiTi and LacZ failed to prove that this region was located in the cell membrane as all plasmid constructions conferred beta-galactosidase activity to *E. coli* and *L. lactis*.

Effect of the modification of the AbiTi:AbiTii ratio

Since both putative proteins are involved in the phage resistance phenotype, we investigated further to determine whether one of them was in limiting concentration. The AbiT system was therefore first cloned into the low-copy plasmid pSA3 (Em$^r$) to generate pED307. Then, DNA fragments encoding one functional and one nonfunctional AbiT proteins gene were cloned into the high-copy plasmid pNZ123 (Cm$^r$) to generate pED209, pED211, pED217, and pED218 (see plasmid construction in Material and Methods). Combinations of these clones were then introduced into *L. lactis* MG1363 to create a condition in which the wild-type AbiTi:AbiTii ratio was modified.

TABLE 5

Site-directed mutagenesis of the C-terminal region of AbiTi

| Plasmid | L 107 | R 108 | V 109 | T 110 | S 111 | S 112 | L 113 | V 114 | A 115 | T 116 | G 117 | I 118 | L 119 | G 120 | L 121 | L 122 |
|---|---|---|---|---|---|---|---|---|---|---|---|---|---|---|---|---|
| pED107 | | | | | | | | | | | | | | | | |
| pED114 | | T | | | | | | | | | | | | | | |
| pED115 | | | | | | | | | E | | | | | | | |
| pED116 | | | | | | | | V | | | | | | | | |
| pED117 | | | | | | | | | | | | | | | R | |
| pED118 | | | | | | | | | | | | | | | | P |

| Plasmid | S 123 | Q 124 | V 125 | G 126 | I 127 | EOP |
|---|---|---|---|---|---|---|
| pED107 | | | | | | $6.9 \times 10^{-6}$ |
| pED114 | | | | | | $1.1 \times 10^{-2}$ |
| pED115 | | | | | | 1.0 |
| pED116 | | | | | | $8.7 \times 10^{-6}$ |
| pED117 | | | | | | 1.0 |
| pED118 | | | | | | 1.0 |

* Hydrophobic residues are in bold.

It was first concluded that the efficacy of AbiT on phage p2 depended on plasmid copy-number since the EOP was much lower ($10^{-8}$) when the wild-type abiT genes were cloned on the high-copy vector pNZ123 (pED209, Table 6). An increase in the level of AbiTi had no effect on the EOP values ($10^{-2}$), whereas an increase of the AbiTii:AbiTi ratio slightly reduced the EOP ($10^{-3}$) (Table 7). These data demonstrates that the arrangement in the wild-type plasmid pED1 guarantees a balanced stoichiometry between AbiTi and AbiTii for maximum antiphage activity.

TABLE 6

Efficiency of plaquing and plaque size of phage p2 with different concentrations of AbiTi and AbiTii

| Plasmids | AbiTi | AbiTii | EOP* | Plaque size |
|---|---|---|---|---|
| pED307, pNZ123 | + | + | $5.4 \pm 2.7 \times 10^{-2}$ | 1 mm |
| pED307, pED209 | +++ | +++ | $\leq 1 \times 10^{-8}$ | — |
| pED307, pED211 | +++ | + | $3.0 \pm 2.6 \times 10^{-2}$ | 1 mm |
| pED307, pED217 | + | +++ | $6.4 \pm 0.8 \times 10^{-3}$ | Pinpoint |
| pED307, pED218 | + | +++ | $5.6 \pm 3.4 \times 10^{-3}$ | Pinpoint |
| pSA3, pED211 | +++ | − | 1.0 | 2–3 mm |
| pSA3, pED217 | − | +++ | 1.0 | 2–3 mm |
| pSA3, pED218 | − | +++ | 1.0 | 2–3 mm |

*n = 3

TABLE 7

EOP values for members of the three main lactococcal phage species

| 936 species | | P335 species | | c2 species | |
|---|---|---|---|---|---|
| Phage | EOP[a] | Phage | EOP[b] | Phage | EOP[a] |
| p2 | $9.5 \times 10^{-6}$ | ul36 | $2.6 \times 10^{-7}$ | c2 | 1 |
| p2k | $1.4 \times 10^{-6}$ | Q30 | $1.6 \times 10^{-7}$ | eb1 | 1 |
| sk1 | $2.1 \times 10^{-5}$ | Q33 | 1 | ml3 | 1 |
| jj50 | $1.9 \times 10^{-5}$ | Φ31 | $1.9 \times 10^{-7}$ | | |
| | | Φ50 | $4.5 \times 10^{-6}$ | | |

[a]LM0231 (pSA3, pED1) as the host
[b]SMQ481 (pED100) as the host

Efficacy of AbiT Against Different Phage Species

The efficacy of plaquing (EOP) the phage resistance mechanism AbiT was determined against members of the three main lactococcal phage species (936, c2, and P335). All members of the 936 species were sensitive to the antiphage system with EOP values ranging from $10^{-5}$ to $10^{-6}$ (Table 7). Proliferation of members of the P335 species was also severely affected by AbiT with the notable exception of phage Q33. However, none of the c2-like phages was AbiT-sensitive. The efficiency to form centers of infection (ECOI) and the burst size of phage p2 (936 species) and phage ul36 (P335 species) were then evaluated with one-step growth curves (Table 8). Only 4–7% of AbiT+ infected cells released phages and the number of virions released was reduced 10- to 12-fold. Severe reductions in the ECOI and the burst size are typical of Abi systems. The fact that the microbiological impacts of pED1, pED100 and pED109 (FIG. 1) were identical confirms that only abiTi, abiTii, and the promoter are required for a complete phage resistance phenotype.

TABLE 8

Microbiological effects of AbiT on phage p2 of the 936 species and phage ul36 of the P335 species

| Phage | Host | EOP* | ECOI* (%) | Burst size* |
|---|---|---|---|---|
| p2 | LM0231 (pSA3) | 1.0 | 100 | 58 ± 14 |
| | LM0231 (pSA3, pED1) | $9.5 \pm 3.9 \times 10^{-6}$ | 6.5 ± 3.5 | 6 ± 1 |
| | MG1363 (pMIG3) | 1.0 | 100 | 87 ± 3 |
| | MG1363 (pED100) | $2.0 \pm 1.2 \times 10^{-6}$ | 5.4 ± 1.5 | 7 ± 1 |
| | MG1363 (pED109) | $2.0 \pm 0.4 \times 10^{-6}$ | 4.2 ± 0.9 | 9 ± 2 |
| ul36 | SMQ481 (pMIG3) | 1.0 | 100 | 342 ± 28 |
| | SMQ481 (pED100) | $2.6 \pm 1.5 \times 10^{-7}$ | 4.5 ± 1.2 | 27 ± 6 |
| | SMQ481 (pED109) | $2.3 \pm 1.9 \times 10^{-7}$ | 4.3 ± 1.2 | 27 ± 16 |

*n ≥ 3

Effects of AbiT on the Phage Lytic Cycle

Figure 4:
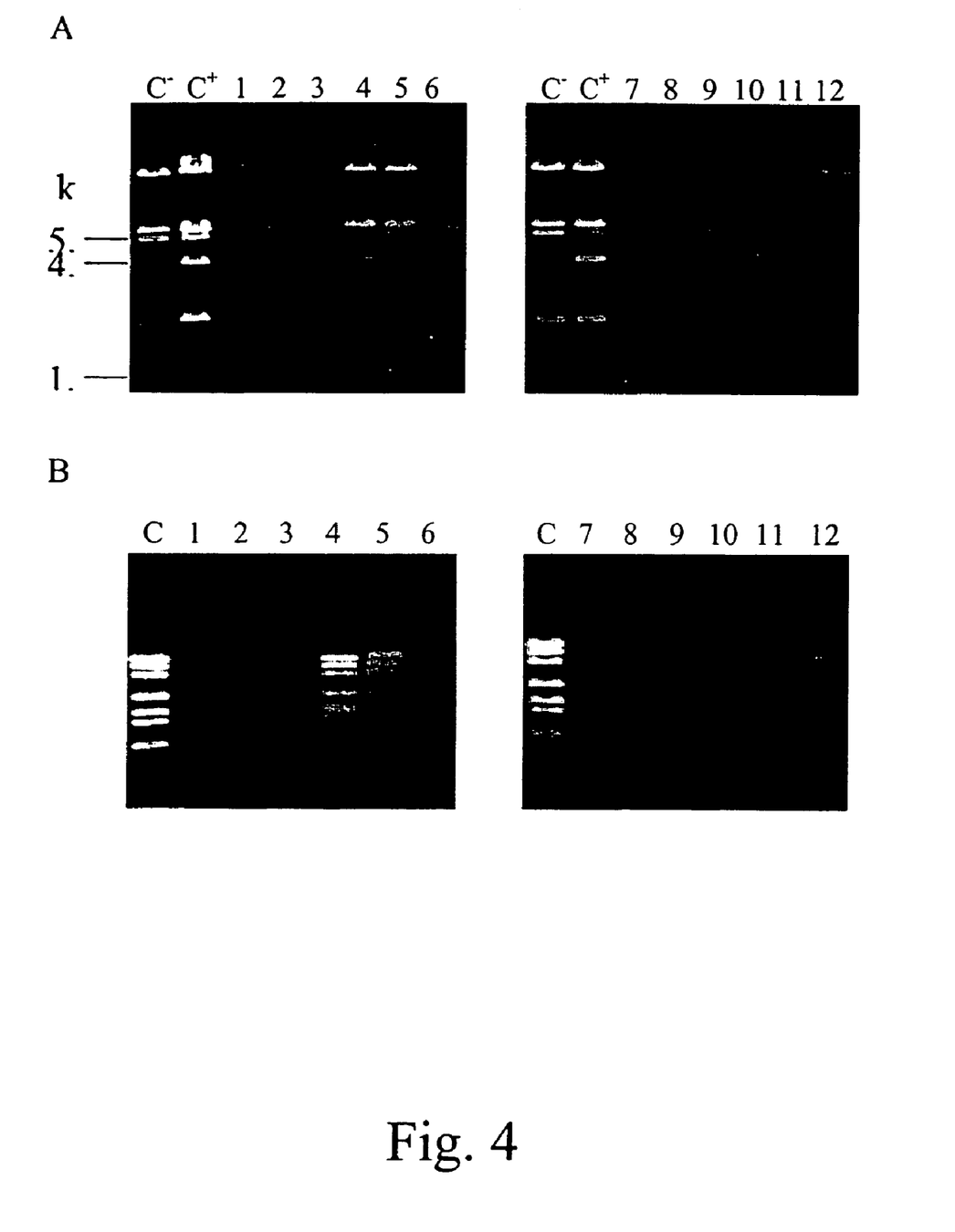
FIGS. 4a and 4B illustrate hybridization of RNA from p2-infected AbiT⁻ (left) and AbiT⁺ (right) cells with the orf35-homologue (A) or the mcp gene (B)
Figure 5:
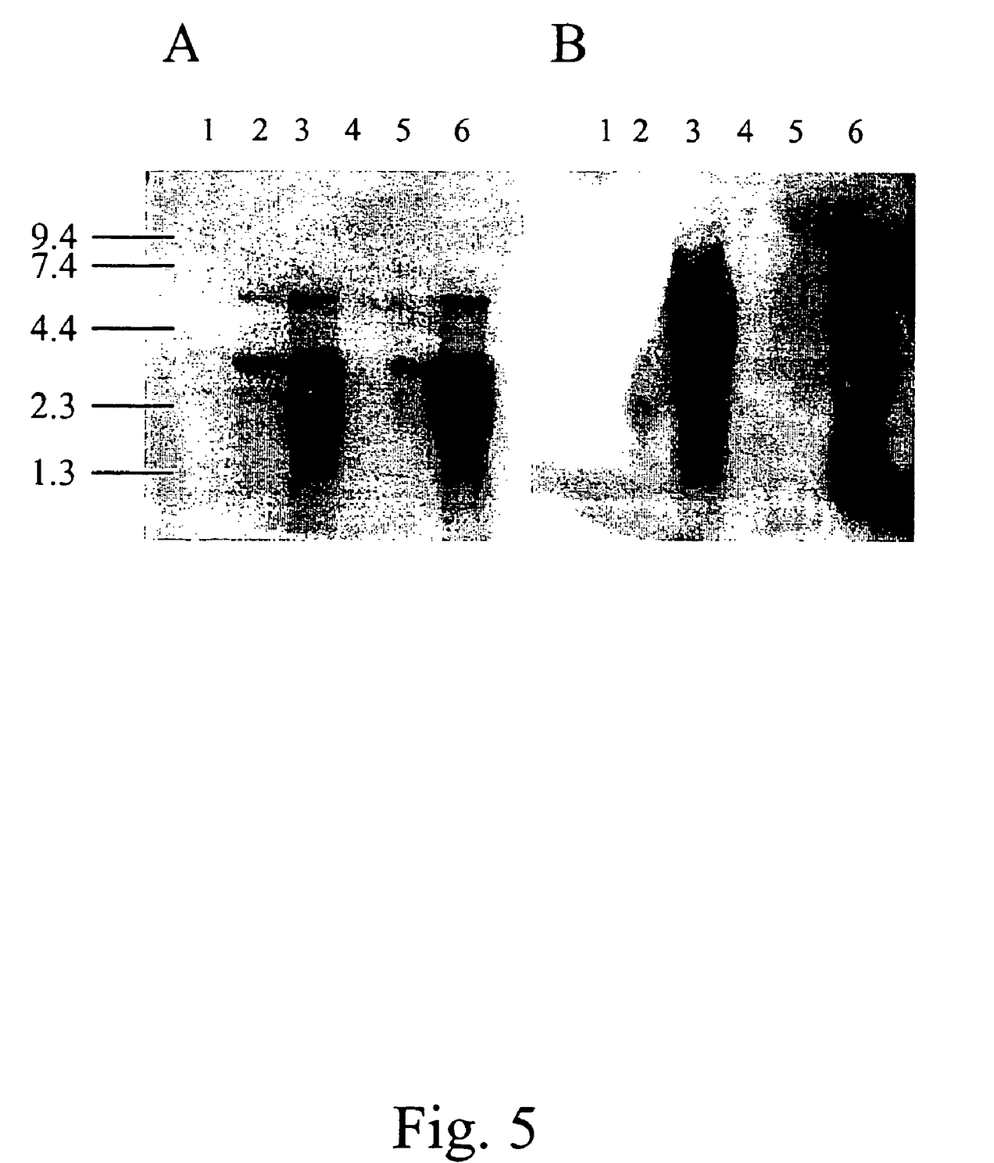
FIG. 5 illustrates hybridization of RNA from p2-infected AbiT⁻ (left) and AbiT⁺ (right) cells with the orf35-homologue (A) and the mcp gene (B)

Total DNA was isolated from sensitive and resistant strains at time intervals during infection with phages p2 (936 species, FIG. 4) or ul36 (P335 species, FIG. 5). For both phages, DNA replication was lowered. In the case of p2, a cos-type phage, DNA was present in its mature (single unit of the linear phage genome) and immature forms (concatemers) in the sensitive strain (FIG. 4, left). The presence of these two DNA forms was visualized through a 5.3-kb EcoRV fragment, which was the product of the 1.3- and the 4.0-kb EcoRV fragments ligated together through their respective cos termini. The mature form (1.3- and 4.0-kb EcoRV fragments) could not be detected in the AbiT-containing strain (FIG. 3A, right). It appears that AbiT affects DNA replication and also prevents effective encapsidation.

Figure 6:
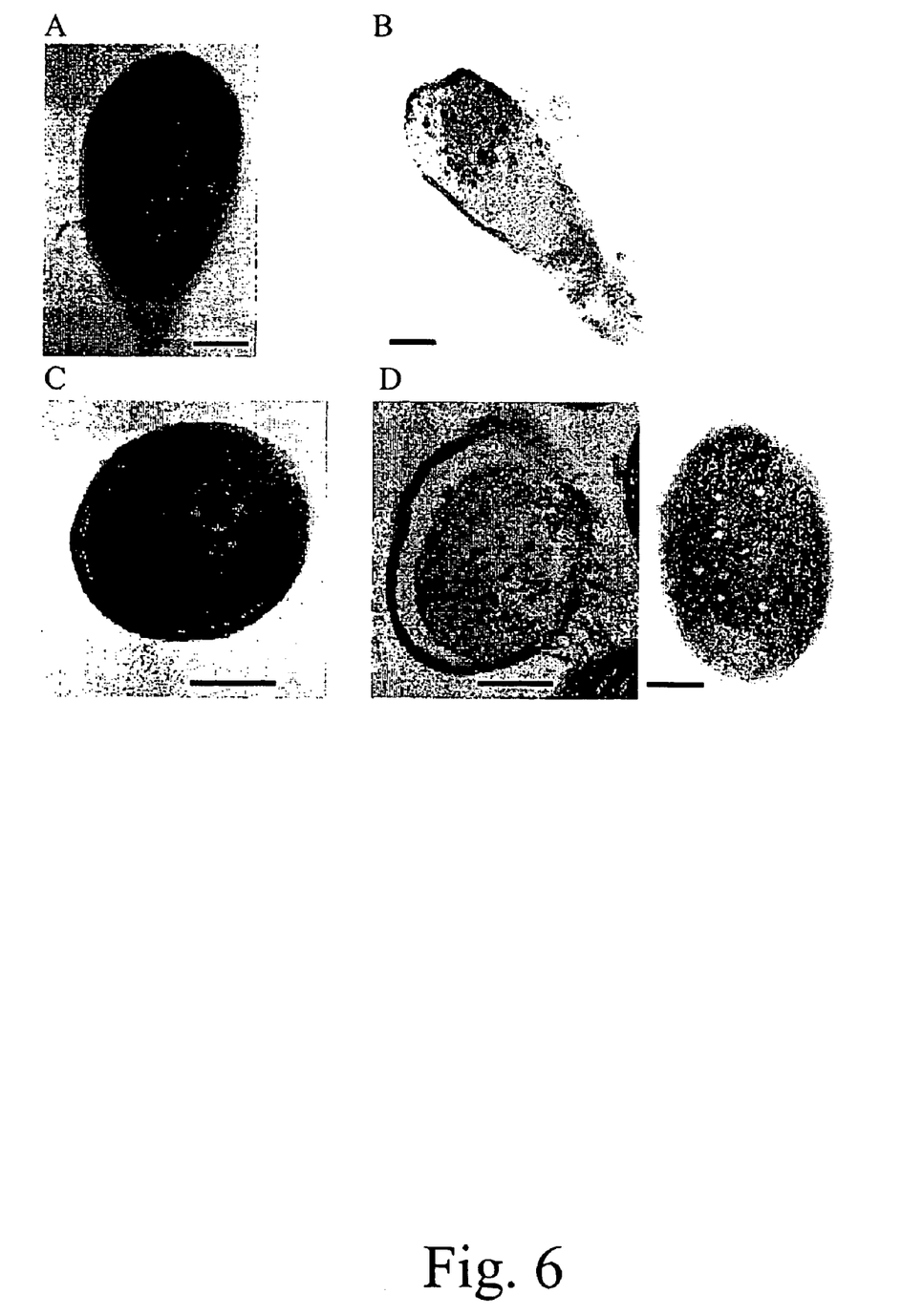
FIGS. 6A to 6D illustrate the monitoring of the lytic cycle by electron microscopy. Panel A and B, *L. lactis* AbiT⁻ infected with phage sk1 at 25 and 45 min, respectively. Panel C and D, *L. lactis* AbiT⁺ cells infected with phage sk1 25 and 45 min, respectively.

Total RNA was also isolated from sensitive and resistant strains at time intervals during infection with phage p2 (936 species). After gel migration, RNA samples were hybridized with two PCR products. The first probe (FIG. 6A) corresponded to an early gene of phage p2, which is identical to orf35 of phage sk1 (936 species). The second probe (FIG. 6B) matched the late gene that encodes the major capsid protein of phage p2. The early and late transcripts were present in the same amount and at the predicted time points for both strains (FIGS. 6A and 6B). This indicates that AbiT does not affect phage gene expression.

Figure 7:
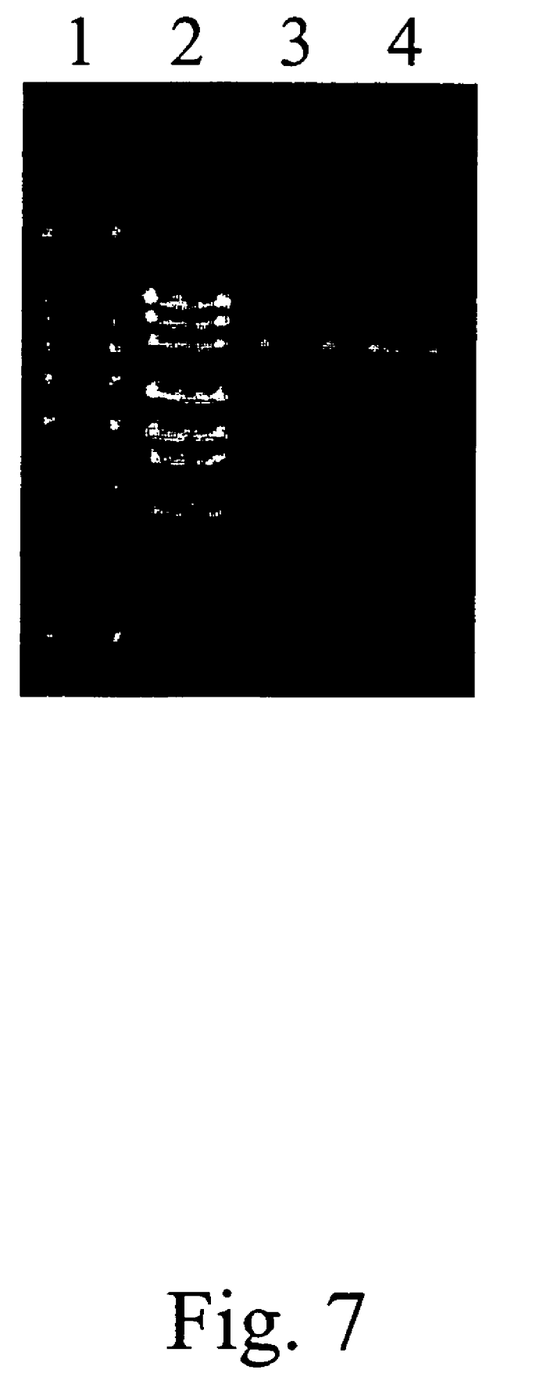
FIG. 7 illustrates EcoRV restriction profile of AbiT-insensitive mutants of phage ul36.

The phage lytic cycle was also monitored at time intervals by electron microscopy in AbiT− and AbiT+ strains. The intracellular course was similar in both infected cells at time 0, 10 and 25 minutes. At this latter time point, the bacterial chromosome was no longer visible and capsid-like structures were found within the cytoplasm of both strains (FIG. 7). Finally at later stages, the infected AbiT− cells lysed and released progeny phages. The fate of the infected AbiT+ cells was less clear as intact cells with empty capsids and lysed cells could be observed, but the latter did not contain filled phage capsids (FIG. 7).

Characteristics of AbiT-Insensitive Phage Mutants

Four plaques of phage p2 were isolated and amplified on pED1-containing strains. Phage DNA was isolated and digested with at least three restriction enzymes. Restriction profiles of the four p2 mutants insensitive to AbiT were identical to those of the wild-type phage. The EOP of the isolated p2 mutants was measured on strains harboring pED109 (low-copy plasmid) and pED209, constructed by cloning the insert of pED109 into the high-copy vector pNZ123. Mutants of p2 were partially insensitive to AbiT as they had EOP values between $10^{-5}$ and $10^{-6}$ with pED209 and of $10^{-1}$ with pED109.

Similarly, 50 plaques of phage ul36 were also isolated and amplified on pED1-containing strains as well as analyzed by restriction profiles. All these phage isolates were insensitive to AbiT (EOP of 1.0), but presented profiles that significantly differed from those of the wild-type phage (FIG. 8). On the basis of their profiles, DNA-DNA hybridization analyses and genome mapping comparisons, 15 to 20 kb of their genome were non homologous to that of ul36, but were related in all mutants. The exchanged region corresponded to the late genes of the phage.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. An isolated protein comprising an amino acid sequence as set forth in SEQ ID NO:1 and an amino acid sequence as set forth in SEQ ID NO:2.

2. An isolated polynucleotide encoding the isolated protein according to claim 1.

3. A bacterium transformed with a vector containing a DNA encoding a first polypeptide having a sequence as set forth in SEQ ID NO:1, and a second polypeptide having a sequence as set forth in SEQ ID NO:2.

4. A method for conferring phage resistance to a bacteria comprising introducing into said bacteria a vector encoding a first protein and a second protein, said first protein having an amino acid sequence as set forth in SEQ ID NO:1 and said second protein having an amino acid as set forth in SEQ ID NO:2.

5. The method as claimed in claim 4, wherein said vector is a plasmid.

* * * * *

SEQUENCE LISTING

```
<160> NUMBER OF SEQ ID NOS: 13

<210> SEQ ID NO 1
<211> LENGTH: 126
<212> TYPE: PRT
<213> ORGANISM: lactococcus
<220> FEATURE:
<221> NAME/KEY: PEPTIDE
<222> LOCATION: (1)...(126)

<400> SEQUENCE: 1

Met Glu Asn Asn His His Asn Asn Lys Glu Lys Asp Thr Asn His Ser
 1               5                  10                  15

Val Ser Val Ser Gly Asn Ala Thr Gly Val Gln Ile Gln Gln Asn Val
                20                  25                  30

Ser Asn Ser Thr Gln Thr Gln Ala Val Asn Glu Val Phe Glu Tyr Glu
            35                  40                  45

Lys Val Leu Glu Val Leu His Glu Ile Ser Asn Phe Gln Gln Met Phe
        50                  55                  60

Lys Asp Thr Tyr Asn Glu Ala Glu Gln Val Leu Asp Leu Leu Asn Gln
 65                  70                  75                  80

Ala Lys Gln Ala Val Thr Asn Arg Glu His Pro Ser Lys Ile Lys Gly
                85                  90                  95

Phe Leu Asn Val Ile Lys Asp Ile Ser Leu Arg Val Thr Ser Ser Leu
                100                 105                 110

Val Ala Thr Gly Ile Leu Gly Leu Leu Ser Gln Val Gly Ile
            115                 120                 125
```

```
<210> SEQ ID NO 2
<211> LENGTH: 212
<212> TYPE: PRT
<213> ORGANISM: lactococcus
<220> FEATURE:
<221> NAME/KEY: PEPTIDE
<222> LOCATION: (1)...(8)

<400> SEQUENCE: 2

Met Gly Lys Ile Val Leu Asp Leu Gln Leu Glu Ala Leu Ser Lys Asp
 1               5                  10                  15

Ser Asp Val Leu Asn Leu Leu Arg Lys Ala Tyr Val Val Ala Arg Lys
            20                  25                  30

Leu Lys Leu Asp Glu Phe Glu Glu Trp Val Asn Ser Glu Leu Asn Gly
        35                  40                  45

Tyr Lys Asp Gly Asn Lys Ile Glu Tyr Arg Lys Val Lys Gly Glu Val
    50                  55                  60

Lys Gly Trp Asn Pro Tyr His Gly Trp Ile Pro Met Ile Met Lys Asp
65                  70                  75                  80

Thr Glu Ile Glu Asn Met Ile Ser Glu His Leu Val Ser Asp Ser Ile
                85                  90                  95

Pro Asn Leu Lys Asn Val Tyr Asp Ser Ala Asn Gly Ser Asn Ala Thr
            100                 105                 110

Leu Gln Phe Asn Ala Gly Met Asn Asn Leu Leu Ser Lys Leu Ser Asp
        115                 120                 125

Phe Asn Thr Lys Tyr Ala Leu Met Ile Ser Ala Asn Gln Ile Tyr Asn
    130                 135                 140

Ile Met Glu Arg Val Arg Asn Ile Val Leu Asp Trp Ser Ile Thr Leu
145                 150                 155                 160

Glu Glu Asn Asp Ile Leu Gly Glu Gly Leu Gln Phe Thr Lys Arg Glu
                165                 170                 175

Lys Asp Ile Ala Val Ser Ser Thr Ile Asn Asn Tyr Thr Asn Asn
            180                 185                 190

Phe Tyr Gly Asp Val Arg Glu Thr Gln Ile Gln Gln Asp Thr Ser Glu
        195                 200                 205

Ser Thr Gln Lys
    210

<210> SEQ ID NO 3
<211> LENGTH: 2227
<212> TYPE: DNA
<213> ORGANISM: lactococcus
<220> FEATURE:
<221> NAME/KEY: misc_recomb
<222> LOCATION: (1)...(2227)
<223> OTHER INFORMATION: Plasmid

<400> SEQUENCE: 3
ctttcaaaag gtgcttttg tctttctagt ttgaaaaata tagtctattt ttttattctt    60
cgtaactcat tatatatact tacaatcaag gctattacta ataagcattc ccatattta    120 ctaaaaatat cttgcccata aaaaatactg aatacagaaa taattaatag agggaattgc   180
cataatagtg actgtatcct tacattttt cttttctgta tcgaaatgat tgtagcaatt   240
aatcctaata taaataatca actagcaatt cgggtcttta ttaaatacta atgattgcat   300 taaaattgc tttttgagat aattgctaaa aagagagga ttctcaaatg gataacaaag    360
atatagagct gattcaacaa atggaaaaca aatatgacac ttttatgcca gtcttaacta   420
```

```
atttaattga tagtgttgaa aaatttaact caatttacaa taactatatt gaattaagaa        480 attttttatgg tagtgaaaaa tggtttgaat atatggaaat tgaaaaaatc ccagtaaaat       540
gtggtgtttt aacagaagac caattatttg atatgattag tgatcataat gaacttcttg       600
gagtattact tgacctaact tcaaaaatgt acaaaaattt ttaaaaatat caaagattca       660
aatatcttaa aaatggtgca ggatacacta cttgatagtt ttcgtgctgg tcgtcgcaat       720
tacaccatct ttcaagtggg gaaagccact ctcttaaggg taagtgatgt catgaaactt       780
aaaaaatcag atgtctttaa tcctgatgga acggttaaac aaaccgcttt tattcatgat       840
caaaaaacag gaaaggcgaa tacgttatat ttgaaaccag tacaacaaga tctagtggtc       900
tatcatgatt ggctggtcca acaaaatctt aattctgagt ggttgtttcc ctcaacgact       960
catatagaga ctattgtgtt gctacaacga gcaaatacgt agaaatcctt tatttcaagc      1020
acttttacaa gcatatcgtc tttactggtg aggggaataa aatcagaaat aaagagatta      1080
aggactatat caatgtttct gtagtgattg atatagagtg tggagataca acaaaataaa      1140
gaatgggatt ataagaaacg gagggacatt atggaaaata atcatcataa caacaaagaa      1200
aaggatacta atcactctgt tagtgtttca ggaaatgcta ctggggttca aattcaacag      1260
aatgtatcta attctacgca aacacaggca gtaaatgaag ttttttgaata cgaaaaagta      1320 ttagaagttt tacacgaaat ttcgaatttc cagcagatgt ttaaagatac ttacggaaat      1380
gaagcggaac aagtattaga tttactaaat caagctaaac aagcagtcac aaacagggaa      1440
catccatcca agataaaagg atttctcaat gtcattaaag acatatcatt aagagttaca      1500
agtagcttag tggcaacagg aatacttggt ctacttagtc aagttggaat ttagaggtag      1560
tacaatggga aaaatagttt tggatttaca actagaagca cttagtaaag atagcgatgt      1620
tttgaattta ttaaggaaag cttatgtagt agcaagaaaa ttaaagttgg atgaatttga      1680
agaatgggtc aatagtgagt tgaacggcta taaagatggc aataagattc ctgaatatag      1740
aaaagttaag ggcgaagtca aagggtggaa cccgtatcat ggttggattc ctatgattat      1800
gaaagatact gagatagaaa atatgatttc agaacattta gtttcagact caatccctaa      1860
tctaaaaaat gtatacgata gtgcaaatgg tagtaatgca acattacagt ttaatgcagg      1920
tatgaacaat ctattatcaa aattgagtga ttttaataca aaatacgctt taatgataag      1980
tgcaaatcaa atatataata ttatggaaag agttcgtaat attgtactag attggtcgat      2040
tactcttgaa gaaatgaca tattaggaga ggggttgcaa tttacgaaaa gagaaaaaga      2100
tattgctgtt tcttcttcaa ctattaataa ttacacgaat aatttctatg gtgatgttcg      2160
agaaacgcaa atacagcaag acacatcaga atctacgcaa aaatagagta atacgatttt      2220
aaggagt                                                                2227
```

<210> SEQ ID NO 4
<211> LENGTH: 380
<212> TYPE: DNA
<213> ORGANISM: lactococcus
<220> FEATURE:
<221> NAME/KEY: gene
<222> LOCATION: (1)...(380)
<223> OTHER INFORMATION: AbiTi

<400> SEQUENCE: 4

```
atggaaaata atcatcataa caacaaagaa aaggatacta atcactctgt tagtgtttca        60
ggaaatgcta ctggggttca aattcaacag aatgtatcta attctacgca aacacaggca       120
gtaaatgaag ttttttgaata cgaaaaagta ttagaagttt tacacgaaat ttcgaatttc      180
```

```
cagcagatgt ttaaagatac ttacggaaat gaagcggaac aagtattaga tttactaaat      240
caagctaaac aagcagtcac aaacagggaa catccatcca agataaaagg atttctcaat      300
gtcattaaag acatatcatt aagagttaca agtagcttag tggcaacagg aatacttggt      360
ctacttagtc aagttggaat                                                  380
```

<210> SEQ ID NO 5
<211> LENGTH: 640
<212> TYPE: DNA
<213> ORGANISM: lactococcus
<220> FEATURE:
<221> NAME/KEY: gene
<222> LOCATION: (1)...(640)
<223> OTHER INFORMATION: AbiTii

<400> SEQUENCE: 5

```
atgggaaaaa tagttttgga tttacaacta gaagcactta gtaaagatag cgatgttttg       60
aatttattaa ggaaagctta tgtagtagca agaaaattaa agttggatga atttgaagaa      120
tgggtcaata gtgagttgaa cggctataaa gatggcaata agattcctga atatagaaaa      180
gttaagggcg aagtcaaagg gtggaacccg tatcatggtt ggattcctat gattatgaaa      240
gatactgaga tagaaaatat gatttcagaa catttagttt cagactcaat ccctaatcta      300
aaaaatgtat acgatagtgc aaatggtagt aatgcaacat tacagtttaa tgcaggtatg      360
aacaatctat tatcaaaatt gagtgatttt aatacaaaat acgcttaatg ataagtgcaa      420
atcaaatata taatattatg gaaagagttc gtaatattgt actagattgg tcgattactc      480
ttgaagaaaa tgacatatta ggagaggggt tgcaatttac gaaaagagaa aaagatattg      540
ctgtttcttc ttcaactatt ataattacac gaataaattc tatggtgatg ttcgagaaac      600
gcaaatacag caagacacat cagaatctac gcaaaaatag                            640
```

<210> SEQ ID NO 6
<211> LENGTH: 33
<212> TYPE: DNA
<213> ORGANISM: lactococcus
<220> FEATURE:
<223> OTHER INFORMATION: PED1.1

<400> SEQUENCE: 6

```
gaattcgaat tcgattataa gaaacggagg gac                                    33
```

<210> SEQ ID NO 7
<211> LENGTH: 32
<212> TYPE: DNA
<213> ORGANISM: lactococcus
<220> FEATURE:
<223> OTHER INFORMATION: PED1.2

<400> SEQUENCE: 7

```
tctagatcta gaccgttttc gtagtatcac gt                                     32
```

<210> SEQ ID NO 8
<211> LENGTH: 34
<212> TYPE: DNA
<213> ORGANISM: lactococcus
<220> FEATURE:
<223> OTHER INFORMATION: PED1.3

<400> SEQUENCE: 8

```
gtcgacgtcg acggtgcttt ttgtctttct agtt                                   34
```

```
<210> SEQ ID NO 9
<211> LENGTH: 25
<212> TYPE: DNA
<213> ORGANISM: lactococcus
<220> FEATURE:
<223> OTHER INFORMATION: R108T

<400> SEQUENCE: 9
gctacttgta actgttaatg atatg                                              25

<210> SEQ ID NO 10
<211> LENGTH: 22
<212> TYPE: DNA
<213> ORGANISM: lactococcus
<220> FEATURE:
<223> OTHER INFORMATION: A115E

<400> SEQUENCE: 10
ttcctgtttc cactaagcta ct                                                 22

<210> SEQ ID NO 11
<211> LENGTH: 22
<212> TYPE: DNA
<213> ORGANISM: lactococcus
<220> FEATURE:
<223> OTHER INFORMATION: A115V

<400> SEQUENCE: 11
ttcctgttac cactaagcta ct                                                 22

<210> SEQ ID NO 12
<211> LENGTH: 22
<212> TYPE: DNA
<213> ORGANISM: lactococcus
<220> FEATURE:
<223> OTHER INFORMATION: L122R

<400> SEQUENCE: 12
acttgactac gtagaccaag ta                                                 22

<210> SEQ ID NO 13
<211> LENGTH: 22
<212> TYPE: DNA
<213> ORGANISM: Artificial Sequence
<220> FEATURE:
<223> OTHER INFORMATION: L112P

<400> SEQUENCE: 13
acttgactag gtagaccaag ta                                                 22
```